US 6,673,095 B2

(12) United States Patent
Nordquist

(10) Patent No.: US 6,673,095 B2
(45) Date of Patent: Jan. 6, 2004

(54) APPARATUS AND METHOD FOR DELIVERY OF LASER LIGHT

(75) Inventor: Robert E. Nordquist, Oklahoma City, OK (US)

(73) Assignee: Wound Healing of Oklahoma, Inc., Oklahoma City, OK (US)

(*) Notice: Subject to any disclaimer, the term of this patent is extended or adjusted under 35 U.S.C. 154(b) by 0 days.

(21) Appl. No.: 09/784,320

(22) Filed: Feb. 12, 2001

(65) Prior Publication Data
US 2002/0111610 A1 Aug. 15, 2002

(51) Int. Cl.$^7$ .......................... A61N 5/067; A61B 18/18
(52) U.S. Cl. ................................ 607/89; 606/9; 606/16
(58) Field of Search ............................. 607/89; 606/9, 606/10, 11, 13–16, 17

(56) References Cited

U.S. PATENT DOCUMENTS

| 4,930,504 A | | 6/1990 | Diamantopoulos et al. | |
| 5,271,079 A | * | 12/1993 | Levinson | 385/46 |
| 5,445,146 A | | 8/1995 | Bellinger | |
| 5,540,676 A | * | 7/1996 | Freiberg | 606/10 |
| 5,755,752 A | | 5/1998 | Segal | |
| 5,766,233 A | | 6/1998 | Thiberg | |
| 5,853,407 A | * | 12/1998 | Miller | 606/9 |
| 5,951,596 A | | 9/1999 | Bellinger | |
| 5,964,749 A | | 10/1999 | Eckhouse et al. | |
| 5,993,442 A | * | 11/1999 | Omori | 606/10 |
| 6,033,431 A | | 3/2000 | Segal | |
| 6,110,165 A | * | 8/2000 | Ota | 606/11 |
| 6,110,195 A | * | 8/2000 | Xie et al. | 606/10 |
| 6,146,410 A | | 11/2000 | Nagypal et al. | 607/88 |
| 6,298,187 B1 | * | 10/2001 | Waarts et al. | 359/115 |

FOREIGN PATENT DOCUMENTS

| DE | 37 29 288 A | 3/1989 | A61N/5/06 |
| EP | 0 421 030 A | 4/1991 | A61B/17/36 |
| EP | 1 112 758 A | 7/2001 | A61N/5/067 |
| WO | WO 97 19725 A | 6/1997 | A61N/5/06 |

* cited by examiner

Primary Examiner—Roy D. Gibson
(74) Attorney, Agent, or Firm—Fellers, Snider, Blankenship, Bailey & Tippens, P.C.

(57) ABSTRACT

An apparatus for the delivery of laser light in a therapeutic environment including: a console; an optical waveguide wherein a first end of the waveguide is configured to expose a biological tissue to energy transmitted through the waveguide; a plurality of laser diodes housed within the console such that the light emitted by each of the diodes will illuminate a second end of the optical wave guide; and a power supply for providing electrical power to each laser diode. Preferably each laser diode is configured to produce a unique wavelength of light. The power supply provides an independently controllable output for each laser such that the exposure, both in terms of intensity and duration, to each wavelength of light may be controlled independently of the exposure to each of the other wavelengths of light.

10 Claims, 3 Drawing Sheets

APPARATUS AND METHOD FOR DELIVERY OF LASER LIGHT

BACKGROUND OF THE INVENTION

1. Field of the Invention

The present invention relates to an apparatus and method for the delivery of laser light. More particularly, but not by way of limitation, the present invention relates to an apparatus and method for the delivery of laser light for therapeutic purposes.

2. Background of the Invention

The use of laser light for therapeutic purposes is well known in the art. For some time relatively high power lasers have been used for surgical purposes such as cutting tissue, vaporizing tissue, cauterizing, and the like. More recently, lower power, less focused lasers have been used to stimulate biological tissue rather than destroy tissue. It has been proven that laser light, thus used, may, among other things, reduce or eliminate chronic pain, promote healing of wounds, and reduce inflamation.

Generally speaking, all light striking a biological tissue is either reflected, transmitted, or absorbed. It has been found that the degree to which a particular tissue reflects, transmits, or absorbs light will vary radically with the wavelength of the light applied to the tissue. Not surprisingly, it has also been found that the biological response of a particular tissue will vary radically with the wavelength of the light applied to the tissue. Furthermore the depth to which a given wavelength of light will penetrate a particular tissue is dependent on the degree to which the tissue is transmissive at the given wavelength.

A number of prior art devices have focused on the use of lasers for such treatments having a wavelength in the near infrared range. For example, U.S. Pat. No. 5,445,146 issued to Bellinger discloses the use of a Nd:YAG laser having a fundamental wavelength of 1064 nanometers with a power level between 100 milliwatts and 800 milliwatts. The Nd:YAG laser is traditionally a pumped laser, excited by an external light source. Such lasers are typically rather cumbersome, relatively expensive, and the output power is somewhat difficult to control. In addition, such lasers are only available with light output at specific wavelengths.

U.S. Pat. No. 5,951,596 also issued to Bellinger discloses the use of either the Nd:YAG laser or, alternatively, an Nd:YLF laser producing energy with a wavelength of 1055 nanometers. As with the Bellinger '146 device, the Bellinger '596 patent discloses only the use of a pumped laser.

U.S. Pat. No. 5,755,752 issued to Segal discloses the use of a semiconductor laser, specifically an Indium Gallium Arsenide (In:GaAs) diode configured for producing energy having a wavelength in the near infrared range, in the range between 1044 nanometers to 2520 nanometers, preferably at 1064 nanometers. The laser diode is relatively small allowing it to be positioned in a wand. While the Segal '752 device overcomes some of the limitations of the devices using pumped lasers, it too only delivers a single wavelength of light to the patient.

U.S. Pat. No. 4,930,504 issued to Diamantopoulos et. al., discloses a cluster probe for biostimulation of tissue having an array of monochromatic radiation sources of a plurality of wavelengths wherein two radiation wavelengths simultaneously pass through a single point. Diamantopoulos teaches that when a tissue is simultaneously exposed to multiple wavelengths of a light, a cumulative, and sometimes synergistic, effect is obtained. Diamantopoulos suggests that this effect is based, in part, on the "mixing" of photons.

While the Diamantopoulos '504 device provides a plurality of wavelengths, it does not provide independent exposure control for each wavelength. Thus, the relative exposure, both in terms of relative intensity and relative duration, between the various wavelengths of light is fixed at the time of manufacture of the device.

It has been shown that the response of a particular tissue to an exposure to light varies based on the wavelength, intensity, and duration of the exposure. Thus, while there are advantages realized in delivering multiple wavelengths of light, to achieve the maximum advantage, the exposure to each particular wavelength must be tailored to, among other things: a) the particular tissue receiving treatment; b) the desired depth of penetration into the tissue for each wavelength of light; and c) the degree of stimulation required.

It is thus an object of the present invention to provide a device for the delivery of laser light which provides a plurality of discrete wavelengths of light each of which strikes substantially the same area on a treated tissue.

It is further object of the present invention to provide independent control for each wavelength of light such that the exposure to each wavelength, in terms of both intensity and duration, may be controlled independently from the other wavelengths of light produced.

It is yet a further object of the present invention to provide a power supply for a laser delivery system which provides multiple output channels, each channel being independently controllable.

SUMMARY OF THE INVENTION

The present invention provides an apparatus and method for the delivery of laser light in a therapeutic environment which satisfies the needs and alleviates the problems mentioned above. The inventive apparatus provides a plurality of discrete wavelengths of light wherein each wavelength is provided by a laser diode, or a group of laser diodes, and the intensity and duration of the light produced at each wavelength are independent of the intensity and duration of the light produced at other wavelengths.

The inventive apparatus comprises: a console; a plurality of laser diodes housed within the console such that the light emitted by each of the diodes will illuminate the input of an optical waveguide; and a power supply for providing electrical power to each laser diode. The output of the optical waveguide is used to deliver the light to a tissue. Preferably, each diode is configured to emit a different wavelength of light.

For purposes of this invention, the term "light" refers to emitted electromagnetic energy (coherent or otherwise) having a wavelength between 100 nanometers and 2600 nanometers. While only a portion of the spectrum is actually visible to the human eye, the entire range exhibits optical properties relevant to the present invention.

Further objects, features, and advantages of the present invention will be apparent to those skilled in the art upon examining the accompanying drawings and upon reading the following description of the preferred embodiments.

DESCRIPTION OF THE PREFERRED EMBODIMENTS

Figure 1:
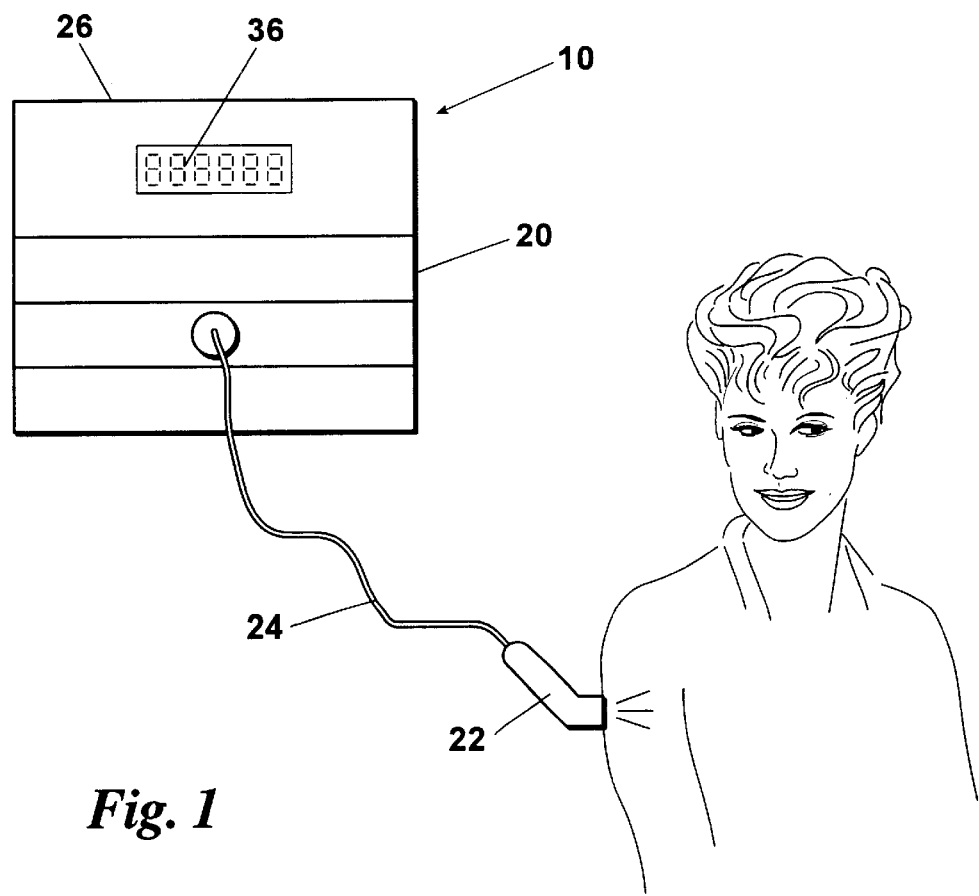
FIG. 1 provides a perspective view of the preferred embodiment of a system for the delivery of laser light in a therapeutic environment.

The present invention provides a new apparatus and method for the delivery of laser light in a therapeutic environment wherein multiple lasers provide illumination of the input end of an optical waveguide such that the light striking the input will include a plurality of discrete wavelengths. Referring first to FIG. 1, a preferred embodiment of a system for the delivery of laser light 10 comprises: a console 20; a hand held wand 22; and an optical waveguide 24 for transmitting the laser light from the console to the wand.

Figure 2:
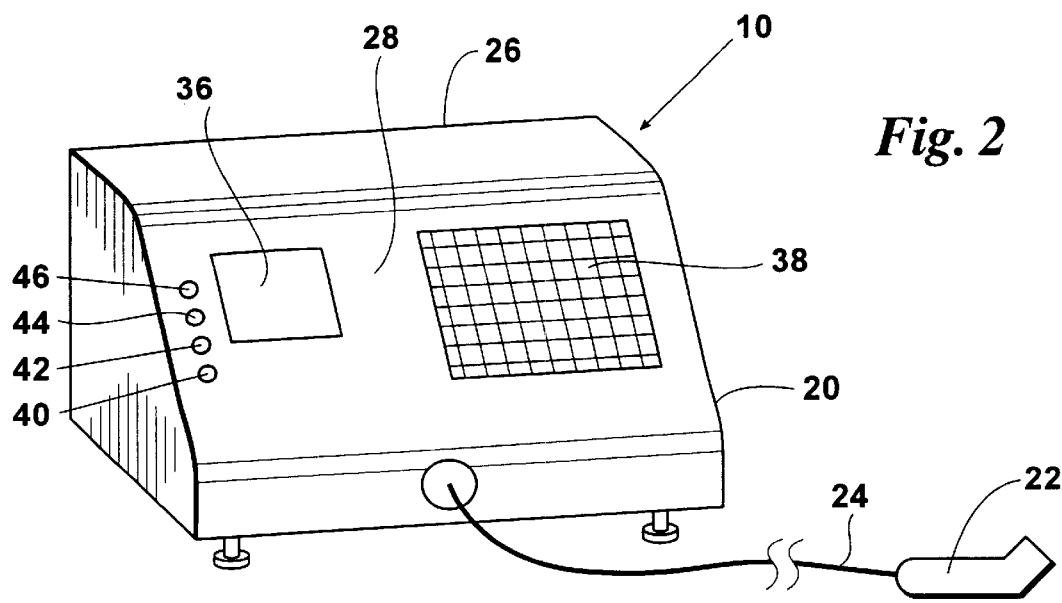
FIG. 2 provides a front view of the system for the delivery of laser light in its general environment.
Figure 3:
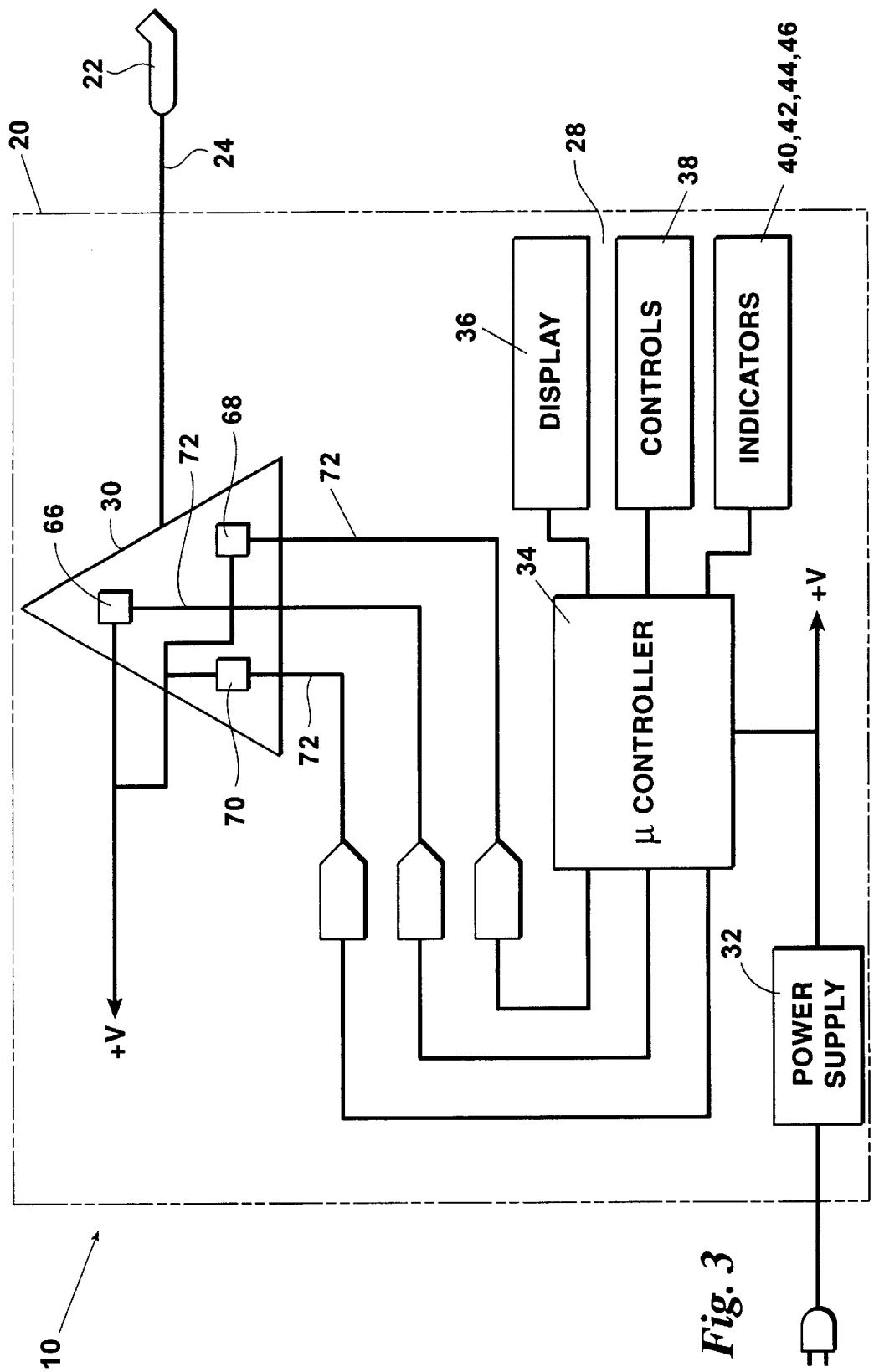
FIG. 3 provides a block diagram of the preferred embodiment of a system for the delivery of laser light.

Referring additionally to FIGS. 2 and 3, console 20 includes: enclosure 26; a user interface 28 displayed on the face of enclosure 26; laser assembly 30 housed within enclosure 26; a controller 34 which controls the operation of laser assembly 30 and user interface 28; and power source 32 for providing electrical power to laser assembly 30 and controller 34. An operator may provide input to the controller through user interface 28 to control the intensity and duration of each wavelength of light within predetermined limits.

Preferably, user interface 28 includes a numeric display 36, a keypad 38, and a series of indicators 40, 42, 44, and 46. Indicator 40 provides a visual indication of whether the console is in a setup mode or an operational mode. In the setup mode, the operator may input the precise exposure the tissue will receive. In this mode, indicators 42, 44, and 46 indicate the feature being programmed by the operator while display 36 provides visual feedback of each number entered by the operator. In the operational mode, indicators 42, 44, and 46 indicate the status of the unit while display 36 provides a display of time remaining for the present treatment.

As will be apparent to one of ordinary skill in the art, display 36 could be implemented in a graphical display such as a cathode ray tube or a liquid crystal display. If display 36 is a graphical display, indicators 40, 42, 44, and 46 could be incorporated into the display.

Figure 4:
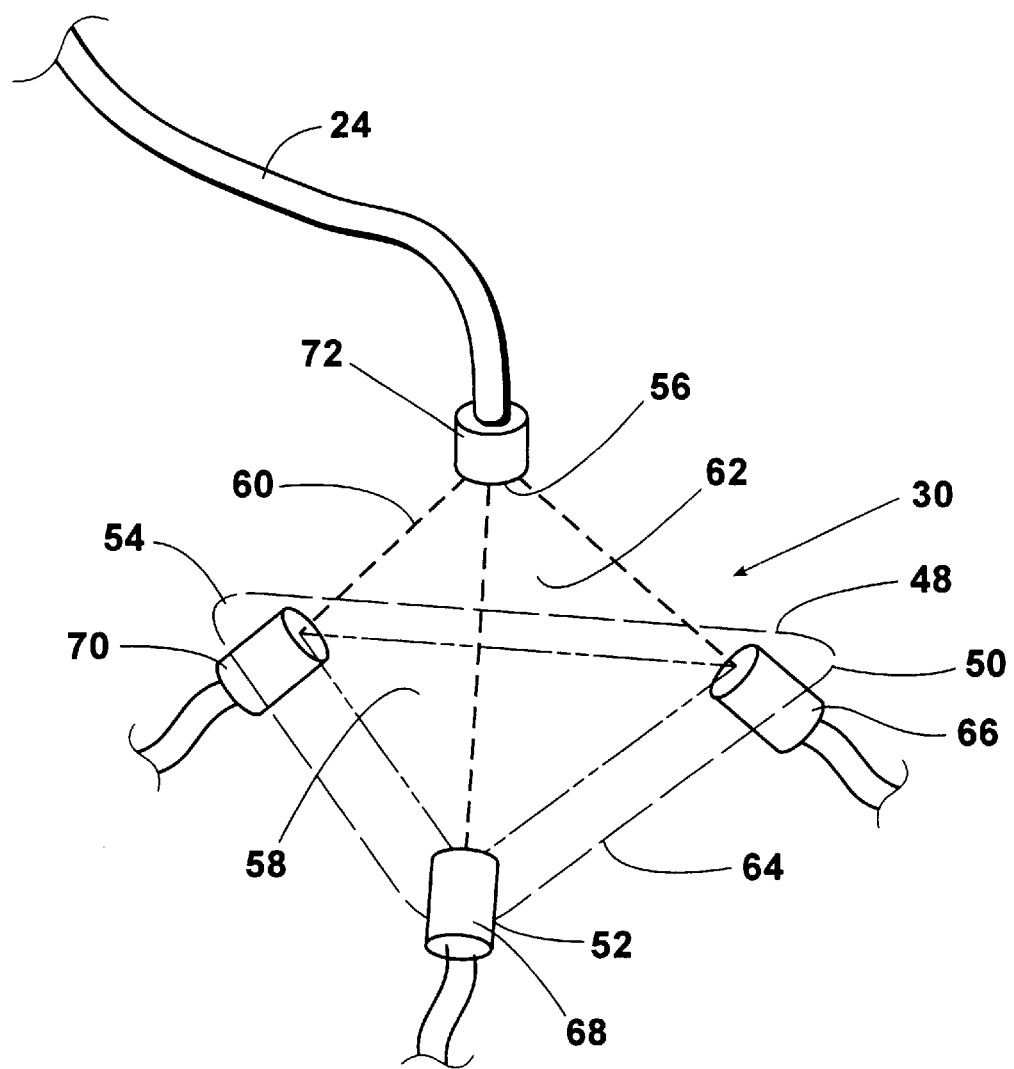
FIG. 4 provides a perspective view of a laser diode assembly incorporated in the system for the delivery of laser light.

Referring now to FIG. 4, laser assembly 30 preferably comprises: a tetrahedral frame 48 having vertices 50, 52, 54, and 56 opposite sides 58, 60, 62, and 64 respectively; laser diode module 66 supported at vertex 50 with the output directed towards vertex 56; laser diode module 68 supported at vertex 52 with the output directed towards vertex 56; laser diode module 70 with the output likewise directed towards vertex 56; and fiber optic connector 72 supported at vertex 56 such that, with a fiber optic cable 24 (FIG. 1) installed at connector 72, the light outputs from diodes 66, 68, and 70 will strike the end of cable 24.

As previously stated, the term "light" is used broadly herein to refer to electromagnetic waves which exhibit optical properties consistent with the present invention and thus, the term "light" is not limited to the visible spectrum.

Laser diodes, as generally known in the art, are semiconductor devices which emit coherent, monochromatic light. Monochromatic, as used herein, refers to light of substantially a single wavelength or light of a narrow range of wavelengths. Laser diodes are available in a variety of wavelengths.

Referring again to FIG. 3, each diode module 66, 68, and 70 preferably includes an intensity input 72 such that the power output of module 66, 68, or 70 may be set with an external voltage. In the preferred embodiment, each module 66, 68, or 70 is capable of outputting up to 20 watts of light. Thus, with a control voltage of zero volts, a module will produce no light. With a control voltage set at a maximum value, a module will output approximately 20 watts. For any control voltage in between zero and the maximum, a module will have an output between zero watts and 20 watts, proportional to the control voltage. Alternatively, a diode laser without an intensity input could instead be used in conjunction with a power supply having a programmable output current.

As noted above, the response of a particular tissue to an exposure to light varies with the wavelength of the light. In addition, the depth of penetration into a particular tissue, or through a tissue to an underlying tissue, is likewise dependent on the wavelength of the light. In order to allow exposure to a beneficial wavelength and to allow penetration to an appropriate depth, preferably each of lasers 66, 68, and 70 provides light at a wavelength different from each of the other lasers 66, 68, or 70. In the preferred embodiment laser diode 66 provides light of a wavelength between 500 nanometers and 700 nanometers. Laser diode 68 provides light of a wavelength between 700 nanometers and 900 nanometers. Finally, laser diode 70 provides light of a wavelength between 900 nanometers and 1300 nanometers. While three diodes are illustrated in the preferred embodiment, two or more laser diodes come within the scope of the invention.

Controller 34 provides digital information to digital to analog converters 76, 78, and 80 to provide the control voltages for diodes 66, 68, and 70, respectively. Controller 34 receives key presses from keypad 38 and drives indicators 40, 42, 44, and 46 as well as numeric display 36.

Optical waveguide 24 is preferably a flexible, fiber optic cable. As described hereinabove, an input end 82 of fiber optic cable 24 is illuminated by the outputs of the laser diodes 66, 68 and 70. The light is transmitted along waveguide 24 until it exits the opposite, output end 84. End 84 is retained in wand 22 such that when wand 22 is placed in contact with a biological tissue, the light emanating from end 84 will illuminate the tissue in a known pattern.

In an alternate embodiment (not shown), optical waveguide 24 includes a plurality of fiber optic fibers. Each fiber is terminated such that an area under treatment receives light from a plurality of angles, thus allowing simultaneous treatment of an entire area, reducing the total time required to expose the area. In addition, exposing from multiple angles would also allow a greater exposure to be delivered to an underlying tissue. Absorption in the outer tissue would occur over multiple paths, reducing the exposure of the outer tissue along any one path. However, the beams could converge at the underlying tissue to increase the power density of the light at the desired depth. For example, the plurality of fibers could terminate at a cuff such that the ends of the fibers were evenly dispersed around the circumference of the cuff. When placed around an elbow, wrist, knee, etc, the light emitted by the group of fibers would illuminate the joint from many different angels. The joint would then receive treatment from all angles simultaneously, thereby reducing the total treatment time for the patient.

In operation, the controller typically activates each laser, one-at-a-time, for a predetermined period of time in a cyclic fashion. The intensity of each laser is also controlled during the activation of laser. By way of example and not limitation, a particular treatment protocol might call for a one second exposure from laser 66 at 50% of maximum power followed by a three second exposure from laser 68 at 30% power followed by a six second exposure from laser 70 at 80% power. A sequence is then repeated in a cyclic fashion until the total exposure has been produced. It should be noted that, as the laser light is absorbed by the exposed tissues, there is heating of the tissues. If such heating is excessive, the exposed cells will be damaged or destroyed. The heat produced in a given tissue at a given depth is easily predicted for a monochromatic exposure. Thus, the intensity of each wavelength may be maximized by activating the lasers individually. If multiple lasers are activated simultaneously, the power output of each laser would have to be reduced due to prevent damage to the tissue due to the cumulative light absorbed from all of the lasers. Thus, lasers 66, 68, and 70 are preferably activated one-at-a-time.

To deactivate a particular laser, controller 34 simply writes a zero to the appropriate digital to analog convertor 76, 78, or 80. A number of alternative methods could be used to selectively activate or deactivate a laser and such methods are within the scope of the present invention. By way of example and not limitation, such methods include providing an electronically actuable switch (e.g., a transistor, a relay, or the like) in series with each laser, providing a mechanical shutter which could be selectively actuated by the controller, or by providing an electronic shutter such as a liquid crystal device.

To setup a treatment protocol, an operator enters the initial intensity of laser 66 through the keypad followed by the first duration of laser 66. The operator then enters the initial intensity of laser 68 followed by the first duration of laser 68. The operator next enters the initial intensity of laser 70 followed by the first duration of laser 70. The operator then enters the total time, or number of cycles, to repeat this sequence. The operator may then enter a second sequence wherein any, or all, of the values previously entered may be modified. Additional sequences may likewise be entered following the same procedure until the entire treatment protocol has been entered. The wand is then applied to the area of the tissue to be treated and controller 34 activates each laser in accordance with the entered protocol.

In addition, commonly used protocols may be permanently stored in memory within the controller to reduce the time required to setup a given protocol and to reduce the opportunity for error in entering the variable information. The operator then merely selects the preprogrammed protocol and begins the treatment.

Thus, the present invention is well adapted to carry out the objects and attain the ends and advantages mentioned above as well as those inherent therein. While presently preferred embodiments have been described for purposes of this disclosure, numerous changes and modifications will be apparent to those skilled in the art. Such changes and modifications are encompassed within the spirit of this invention.

What is claimed is:

1. A system for the delivery of laser light in a therapeutic environment comprising:
   a frame;
   an optical wave guide having an input end and an output end, said input end secured at a point on said frame; and
   a plurality of laser diodes, each laser diode of said plurality of laser diodes producing a substantially monochromatic output and said each laser diode being secured on said frame such that said monochromatic output directly illuminates said input end,
   wherein said plurality of laser diodes will produce a plurality of discrete wavelengths of light.

2. The system for the delivery of laser light of claim 1 further comprising a wand, wherein the output of said optical waveguide terminates in said wand such that when said wand is in contact with a biological tissue, the light emitted at said output will illuminate a known area of said tissue.

3. The system for the delivery of laser light of claim 1 wherein said optical waveguide comprises a fiber optic cable.

4. The system for the delivery of laser light of claim 1 further comprising a controller having a plurality of outputs,
   wherein for each laser diode of said plurality of laser diodes, there is a corresponding output of said plurality of outputs, and
   wherein the intensity of the light produced by said each laser diode may be controlled by said corresponding output.

5. The system for the delivery of laser light of claim 1 wherein each laser diode of said plurality of laser diodes produces light of a different wavelength than the light produced by any other laser diode of said plurality of laser diodes.

6. A system for the delivery of laser light in a therapeutic environment comprising:
   a housing;
   a plurality of lasers secured in said housing, all of the individual lasers of said plurality of lasers aimed at a common point, said plurality of lasers configured to produce a plurality of wavelengths of light such that each wavelength of said plurality of wavelengths may be enabled independently of each of the other wavelengths of said plurality of wavelengths of light; and
   a controller having a plurality of outputs, said plurality of outputs in electrical communication with said plurality of lasers to selectively enable each wavelength of said plurality of wavelengths of light.

7. The system for the delivery of laser light of claim 6 further comprising:
   a fiber optic cable having an input secured at said common point and a fiber optic output; and
   a wand, said fiber optic output secured in said wand such that when said wand is placed in contact with a tissue and at least one laser of said plurality of lasers is enabled, said output will illuminate a known area of said tissue.

8. A method for the delivery of laser light in a therapeutic environment for the treatment of pain, or to expedite wound healing, including the steps of:
   (a) aiming a plurality of lasers directly at an input to an optical waveguide, said waveguide also having an output;
   (b) aiming said output of said optical waveguide at a biological tissue for the purpose of treating pain within said biological tissue, or promoting the healing of a wound within said biological tissue; and
   (c) sequentially activating each laser of said plurality of lasers, one at a time, for a predetermined period of time.

9. The method for the delivery of laser light of claim 8 wherein step (c) includes the steps of:
   (c)(i) sequentially activating each laser of said plurality of lasers, one at a time, for a predetermined period of time;
   (c)(ii) repeating step (c)(i) for a predetermined number of times.

10. The method for the delivery of laser light of claim 8 wherein the power output of each laser is controllable and wherein step (c) further comprises the steps of:
   (c) sequentially activating each laser of said plurality of lasers, one at a time, at a controlled, predetermined output power, for a predetermined period of time.

* * * * *